United States Patent [19]

Miller, Jr. et al.

[11] 4,148,610

[45] Apr. 10, 1979

[54] BATCH PREPARATION OF SAMPLES BY DILUTION

[75] Inventors: Theodore E. Miller, Jr.; Kenneth M. Cabala, both of Midland, Mich.

[73] Assignee: The Dow Chemical Company, Midland, Mich.

[21] Appl. No.: 892,567

[22] Filed: Apr. 3, 1978

[51] Int. Cl.$^2$ ............................................... G01N 1/14
[52] U.S. Cl. ................................ 23/230 A; 73/422 R; 141/7; 141/59; 422/81; 422/100; 422/103
[58] Field of Search ....................... 73/422 GC, 422 R; 23/259, 230 A, 253 A, 253 R; 137/205; 141/7, 59

[56] References Cited

U.S. PATENT DOCUMENTS

| | | | |
|---|---|---|---|
| 3,028,225 | 4/1962 | Sheen | 23/253 R |
| 3,401,565 | 9/1968 | Stoll et al. | 73/422 GC |
| 3,511,080 | 5/1970 | Roof | 73/422 GC X |
| 3,827,302 | 8/1974 | Sato | 73/422 GC |
| 3,921,439 | 11/1975 | Burns | 23/253 R X |
| 4,036,063 | 7/1977 | Roof et al. | 73/422 GC |

Primary Examiner—Morris O. Wolk
Assistant Examiner—Arnold Turk
Attorney, Agent, or Firm—Burke M. Halldorson

[57] ABSTRACT

In the automated, batch preparation of diluted samples, i.e., the preparation of sample/diluent aliquots of repetitively and exactly maintained fixed ratio, metered diluent is pneumatically introduced into a vented mixing chamber, using the principle of gas pressure drop in the dynamic or flowing condition to deposit and entrap the diluent in the chamber. The diluent is thus suspended on the head of a moving gas column that continues to pass through the diluent, producing bubbling agitation. Following the introduction of metered sample by a preferred technique, pressure is equilibrated, producing a momentary quiet condition, and is then reversed, compressing the column of supporting gas underneath the aliquot, and displacing the aliquot into a remote injection loop, and ultimately onto an analytical instrument for testing. The technique permits direct, successful immersion, as an illustrative example, of 2,4-dichlorophenol sample, process stream temperature 180° C., into isopropyl alcohol diluent, boiling point 82° C.

4 Claims, 6 Drawing Figures

BATCH PREPARATION OF SAMPLES BY DILUTION

FIELD OF THE INVENTION

The invention relates to the field of automated process monitoring and analytical testing. More specifically, the invention relates to a general purpose batch dilution system for efficiently preparing analytically suitable sample/diluent aliquots of exacting fixed volume and fixed ratio.

BACKGROUND OF THE INVENTION

Sample preparation for analytical testing frequently, if not most typically, requires sample dilution under exacting conditions. Most important to an automated batch dilution sample preparation system is the factor of repeatability. Thus, it is required for analytical precision that the sample/diluent ratio be fixed and maintained exactly.

Typical prior art systems that depend on exacting tolerances to fix sample diluent ratios, including most commonly, precision metering pumps, capillary flow control devices, critical stream valving devices and the like, are generally, if not characteristically, sensitive to minute flow irregularities. As such, adequate precision control typically requires frequent fine adjustments to balance and establish a fixed flow ratio. Consequently, less than entirely adequate suitability is shown in respect to the performance desired for a generally unattended and automated process sample taking and sample preparation system.

Also, in cases where the diluent is flammable or toxic to the environment, or from an expense standpoint, since analytical grade materials are typically specified, it will be observed that sample preparation systems, as devised in the past, frequently require excessive diluent waste. Thus diluent drains are generally observed as a part of such systems. This condition, quite apparently considered necessary for utility in quite a large number of prior systems, is objectionable standing alone, and even much more so for largely unattended on-stream process applications.

THE INVENTION

The invention departs substantially from prior automated sampling and sample preparation systems. Its design, more specifically employs pneumatic extraction or emptying of a diluent metering loop, and thus transfer of a precisely metered volume of diluent from the loop to a sample/diluent mixing cell. The loop is intermittently filled by connecting a hydrostatic head or column of diluent to each end of the loop. One column serves as the diluent refill source, and the other, or the displacement column, defines a headspace that is periodically evacuated by an aspirator. Intermittent operation of the aspirator thus displaces gas previously entrapped in the diluent loop (as a part of the pneumatic diluent loop emptying step) thus raising the diluent level in the displacement column and ultimately extracting the gas and simultaneously filling the loop. The mode is highly suited to an attendance free, exactly repetitive, automated function. Absolutely no appreciable diluent is wasted and precise metering of the diluent batches or aliquots (usually about 1–3 cc volume) is achieved.

A further aspect of the invention is the mode by which the diluent and sample are combined and mixed. The principle utilizes pneumatically induced transfer of the above precisely metered diluent aliquot along a relatively narrow I.D. tube to a sample/diluent mixing cell. The narrow I.D. tube minimizes cavitation, and cooperatively with the expanded volume of the sample/diluent cell size, deposits the diluent with good stability and reliability into the mixing cell by the principle of pressure drop under the dynamic or flowing condition. The metered diluent is thus suspended on a moving column of air or gas, that continues to pass through the diluent, producing bubbling agitation.

A slide valve subsequently withdraws a precisely metered amount of sample into the mixing chamber, and into contact with the agitated diluent. Immersing is near immediate and under the optimum condition of agitation, thus promoting rapid and complete dissolution of the sample in the diluent. Gas flow is then ceased and the sample/diluent is allowed to momentarily rest to promote the escapement of entrapped gas. The sample/aliquot is supported for the momentary condition on a static gas column. Gas pressure is subsequently reversed on the mixing cell, consequently compressing the aliquot against the supporting gas column, and by gas compression principles, compressing the column, and thus displacing the aliquot into a remote injection loop, and ultimately onto a suitable instrument for analysis. The last mentioned mode of transporting the aliquot permits convenient pass-through and flushing of the injection loop, such as on an alternate basis with sampling.

Yet a further detailed description of the invention is given below in respect to the preferred embodiment to be read in conjunction with the accompanying drawing wherein.

DETAILED DESCRIPTION OF THE INVENTION

Figure 1:
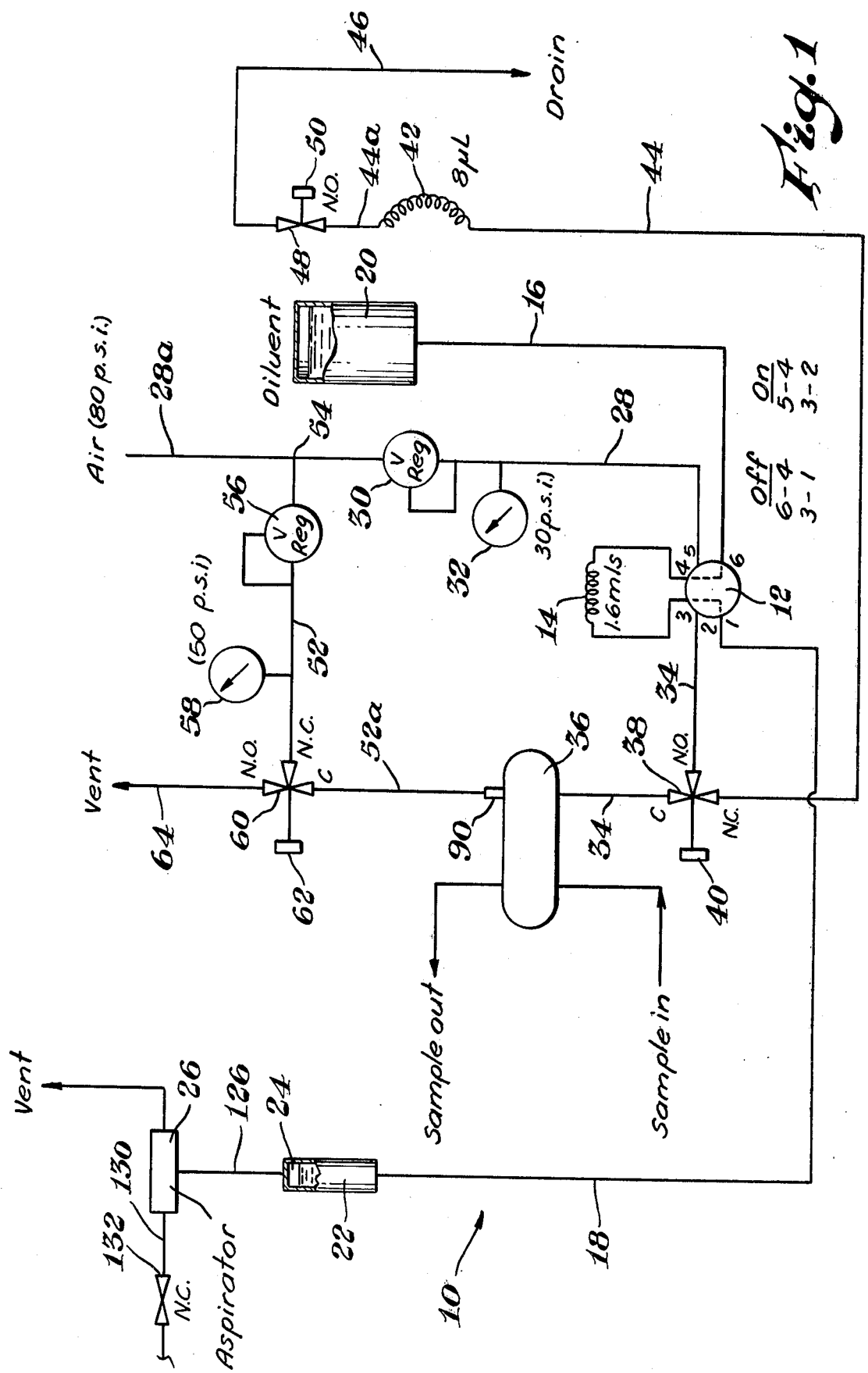
FIG. 1 is an elevational view showing in schematic and diagrammatic detail, preferred apparatus constructed according to the principles of the invention.

Apparatus generally designated by reference numeral 10, in FIG. 1, is constructed to employ the principles of the invention, and includes a double acting, dual 3-way valve 12, preferably made up of a pair of interconnected 3-way slide valves, Product Code No. 201-54 from Altex Corporation (operated by a suitable solenoid pilot valve, not shown, preferably an Asco Company Product Code No. 8345-C1 brass 4-way valve). In the "Off" 6-4, 3-1, position, i.e., loop refilling position, valve 12 connects the opposite ends of a 1.6 milliliter diluent metering loop or metering chamber 14 to a pair of hydrostatic columns or column means 16, 18. The column means 16 comprises an elevated container 20 filled with replenishing diluent, and an associated $\frac{1}{8}''$ stainless steel line, standard wall thickness, leading between container 20 and valve 12. The opposite column means 18 comprises a like stainless steel line leading ultimately to an elevated diluent displacement head in the form of a ⅛" diameter pipe nipple 22, which defines a headspace 24. The headspace in turn is connected to an aspirator 26 shown separately in FIG. 3, and described hereinafter.

In the energized 5-4, 3-2 position, column means 16, 18 are blocked, and the loop is alternately valved to a connection between a pneumatically pressurized gas inlet line 28, controlled by a pressure regulator valve 30 and gauge 32, and a gas outlet line 34. Lines 28, 34 are preferably ⅛", 0.031 I.D., Teflon ® tubing, except for segment 28a, of line 28, which is preferably ¼" tubing. The outlet line 34 leads ultimately to a sample preparation cell 36 (also described hereinafter with respect to FIG. 2) through a 3-way valve 38, also preferably a Product Code No. 201-54 valve, from Altex Corporation, and controlled by a solenoid 40. The inscription "C" as used in the drawing designates the common port, and "NO" and "NC", the normally open and normally closed valve ports, respectively. Valve 38 in the non-energized position thus provides normally open communication between loop 14 and sample preparation cell 36, and in the energized position, this connection is blocked and the sample preparation cell is provided temporary connection to a sample/diluent injection loop 42 through line means 44. The injection loop ultimately leads to a drain line connection 46 through a normally open 2-way valve 48, operated by solenoid 50, and preferably comprising a Product Code No. 201-53, Altex Corporation valve. Line means 44 may comprise 1/16 " Teflon tube except for its segment 44a, between loop 42 and valve 50, which is preferably ⅛". The latter forms an enlarged pneumatic compression chamber, the purpose for which is made evident hereinafter.

Pressured pneumatic line 28 includes a branched line 52 commencing at a T-connection 54 and that leads ultimately also to the sample preparation cell, connecting to the top side thereof. The branched line 52 also preferably ⅛" tubing, is controlled independently by a second pressure regulator valve 56 and gauge 58 and provides on-off pressurized gas supply to the sample preparation cell through a 3-way valve 60 (of preferably like design to valve 38) and which is operated by a solenoid 62. As the inscription in the drawing shows, branched line 52 is normally closed except as to its segment 52a, which provides through valve 60, a normally open communication between cell 36 and a vented line 64.

Figure 2:
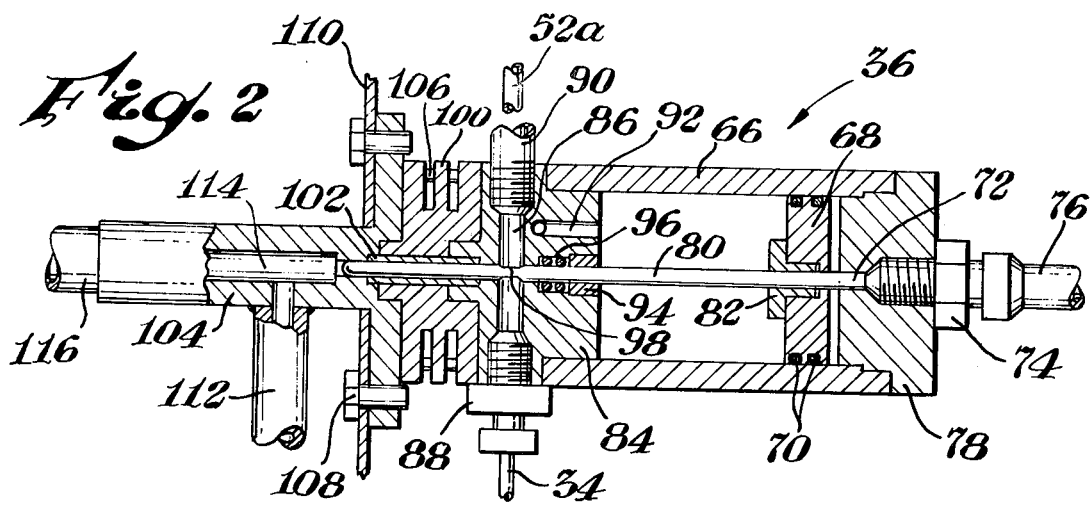
FIG. 2 is a detailed view, in cross-section, of a portion of the apparatus of FIG. 1, depicting the sample/aliquot mixing cell, and associated sample extracting valve member used therein.

Referring now to the sample preparation cell, and FIG. 2, the cell comprises an air cylinder sleeve 66 containing an air cylinder piston 68. The piston is movably sealed to sleeve 66 by plural O-rings 70, and is depressed through pneumatic pressure introduced through a port 72, connector means 74, and air pressure line 76, the port 72 being defined in a sleeve end cap 78 closing one end of air cylinder sleeve 66.

A slidable stem 80 at one end is connected to piston 68 by means of a connector 82. Its opposite end is slidably carried in a series of elements, commencing with a second sleeve end cap 84 closing the opposite end of air cylinder sleeve 66. Cap 84 defines a vertical sample-/diluent mixing chamber or cell 86 (length 2.375", diameter 0.250", volume 1.6 milliliters). The mixing chamber, at its entrance, is attached through connector means 88 with line 34 (I.D. 0.031 inch) ultimately leading to metering loop 14; and at its exit or upper end is attached through means of a ⅛" stainles steel pipe nipple 90 to line 52a, and leads ultimately to vent 64, or pressurized branch line 52, depending on the position of valve 60.

Cap 84 further defines a right angle port 92, through which pneumatic pressure is introduced to return the piston head, thus slidably retracting the stem. The stem extends through the axis of cap 84, guided in a seal retainer 94, and is sealed by plural O-rings 96. In the extreme retracted position, it defines a precisely sized groove 98, (volume 5 μl) which dwells in mixing chamber 86.

A thermal spacer 100 coaxially contains an outer seal element 102, in which stem 80 is slidably supported. A branched end fitting 104 is attached to the assembly immediately axially outwardly of thermal spacer 100 by fastener elements 106. The latter commonly join the end fitting and thermal spacer to cap 84. Separate fastener means 108 mount the assembly to a suitable bracket 110. End fitting 104 defines a sample-in branch 112 which routes sample to a passage 114 which is axially aligned with and receiving of stem 80 (in the piston depressed position). The continuously flowing sample is returned through a second branch or sample-out branch 116 of end fitting 104. The described sample preparation cell is closely structurally similar in design to what is commercially available under the trade name Bendix Liquid Sample Injection Valve, Product Code No. 5518022, Bendix Corporation, and with suitable modifications, this off-the-shelf item may be employed in the distinguishing mode of the invention.

Figure 3:
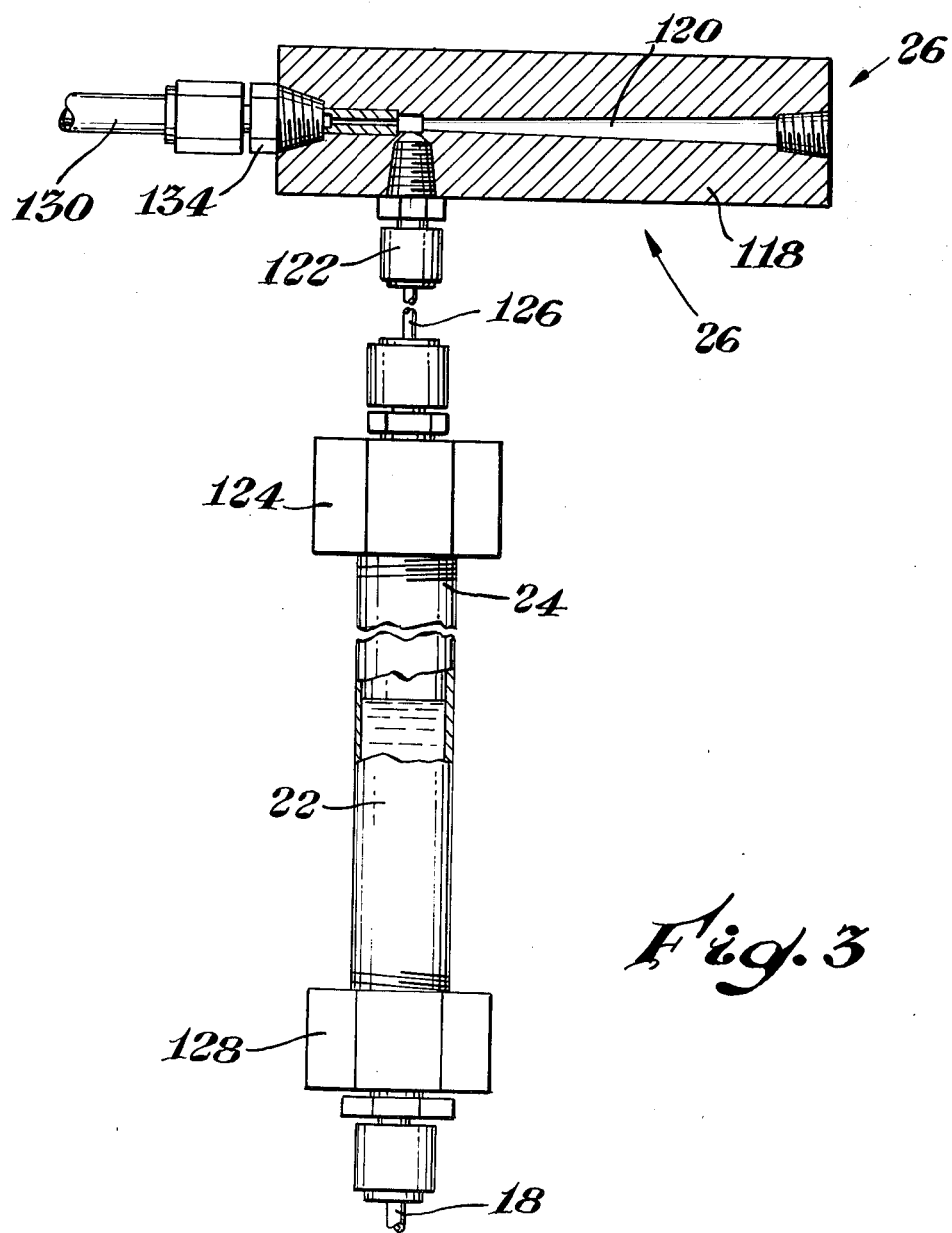
FIG. 3 is similar to FIG. 1, only showing the preferred detail of the diluent displacement column and the aspirator used in conjunction with such column.

The aspirator, see FIG. 3, preferably from Lockwood and Malorie, Inc., includes an aspirator body 118, that defines an axially positioned venturi throat passage 120. The venturi throat passage communicates with the headspace 24 of pipe nipple 22, through connector means 122, 124 and line segment 126. The pipe nipple 22, in turn, is attached to diluent column means 18, through connector means 128, and thus ultimately with metering loop 14 in the "OFF" 6-4, 3-1 position of valve 12. The aspirator is operated by in-fed pressurized air provided through pressurized line 130, controlled by a normally off 2-way solenoid valve 132, and attached to the aspirator through connector means 134.

Operation

In relation now to the operation of the apparatus disclosed, supra, as an arbitrary point of reference, the cycle may be considered to commence with valve 12 in the 6-4, 3-1 non-energized position. At this moment, metering loop 14 is filled with diluent, from the preceding cycle, and is connected to diluent column means 16, 18. The air-line pressure from regulator 30 to mixing chamber 86 is blocked off at valve 12. Regulator 56 similarly is at the static condition with line 52 blocked at vlave 60, and the gas pressure within the mixing chamber 86 is ambient since vent 64 is open.

Filling the Mixing Chamber

Valve 12 is energized to the "ON" 5-4, 3-2 position, disconnecting the metering loop from the column means 16, 18 whereby a discrete amount of diluent, 1.6 milliliters in this example, is captured in the loop. By connection with the pressurized in-feed line 28, the contents of the loop are thus emptied and transported along line 34, through the normally open branch of valve 38, and into the sample/diluent mixing chamber to be ultimately combined with sample. The small line size, I.D. 0.031 inch, promotes plug flow with minimal or no cavitation. In addition, a pressure drop in the dynamic or flowing condition (caused by the respective size of line 34 to mixing chamber 86) is created at the entrance to the mixing cell, depositing the sample reliably therein, under a state of continually induced bubbling agitation. The gas pressure after traversing and bubbling through the diluent is dispelled through vent 64.

Stem 80 is next introduced into the sample stream by depressing piston 68 and it is then retracted into a position placing groove 98 in the mixing chamber. The stem as it is retracted through outer seal 102 is wiped, thus extracting from the stream a precise volume of sample (5 μl) in this example) which is rapidly dissolved in the agitated diluent.

Valve 12 is then returned to the 6-4, 3-1 position, blocking the gas pressure from line 34, and returning the metering loop to its connection with hydrostatic column means 16, 18. The sample/diluent aliquot is thusly supported on a generally static column of air for a momentary dwell period (about 5-10 seconds) permitting entrapped gas bubbles to escape. Following sufficient dwell, valves 38, 60 are simultaneously energized, blocking vent 64, and pressurizing line segment 52a. Simultaneously, valve 38 blocks line 34, and opens the communication between mixing chamber 86 and injection loop 42 along line 44. The sample/aliquot is thus displaced by the resulting unbalanced pneumatic forces, and either captured in injection loop 42 or flushed through the loop and passed to drain, depending on the position of valve 50. In the first mentioned mode, the gas is compressed into the expanded tube segment 44a, thus accurately locating the aliquot in injection loop 42. An alternating sampling/flushing cycle is recommended for optimum precision.

The act of the injection, i.e., of the aliquot captured in injection loop 42, may be used as the command to commence the succeeding sample preparation step. Preceding this command, aspirator 26 is momentarily operated by energizing valve 132, thus reducing the gas pressure in headspace 24 of the displacement column. The relatively small line or column 18, preferably I.D. 0.062 inch, displaces the entrapped gas bubbles from the metering loop into pipe nipple 22, and the displacing medium, i.e., diluent from supply column 16 refills the loop, conveniently, and without waste of diluent whatsoever since levels equilibrate when aspiration ceases. Preferably all energization functions of the valves used in the apparatus are motivated by a series of interconnected electrical timers, of off-the-shelf construction, through the illustrated solenoids, and interconnected with a signal generated from the activity of the injection loop 42, as mentioned supra, which commences each thusly timed cycle.

Figure 4:
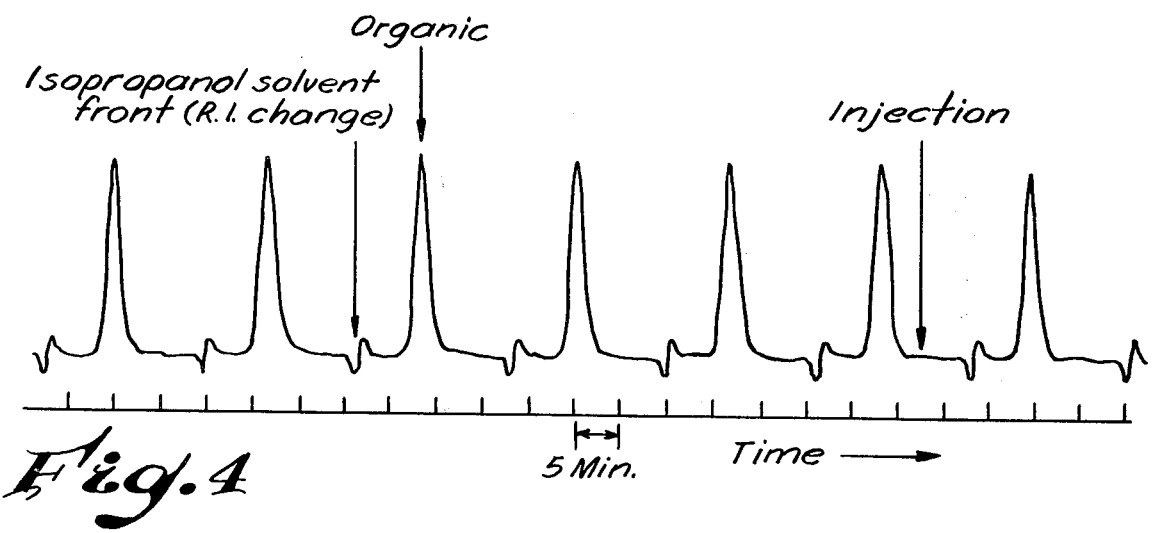
FIGS. 4–6 reproduce certain graphs generated to demonstrate the precision of the sample batch dilution system of the invention, using samples of known standards to judge reliability and repeatability of performance.
Figure 5:
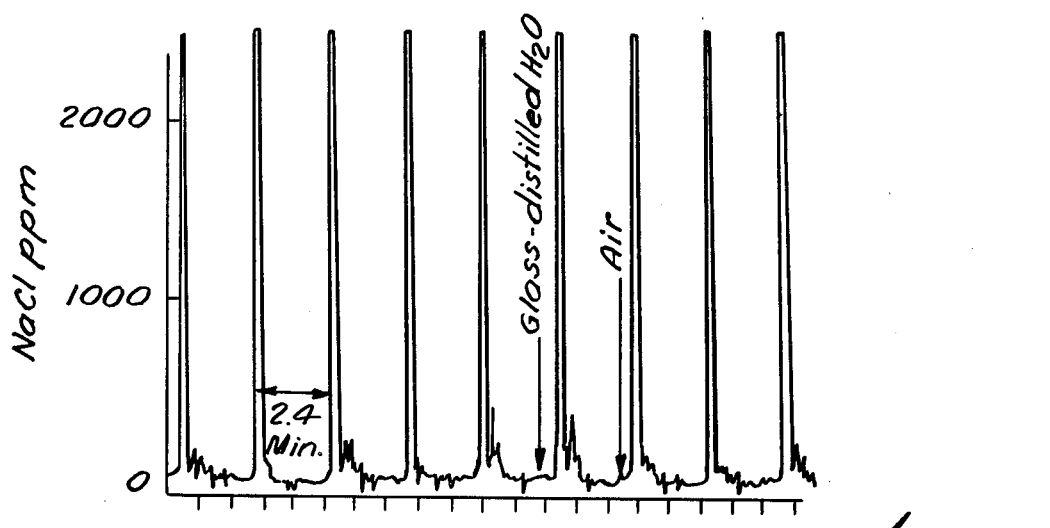
Figure 6:
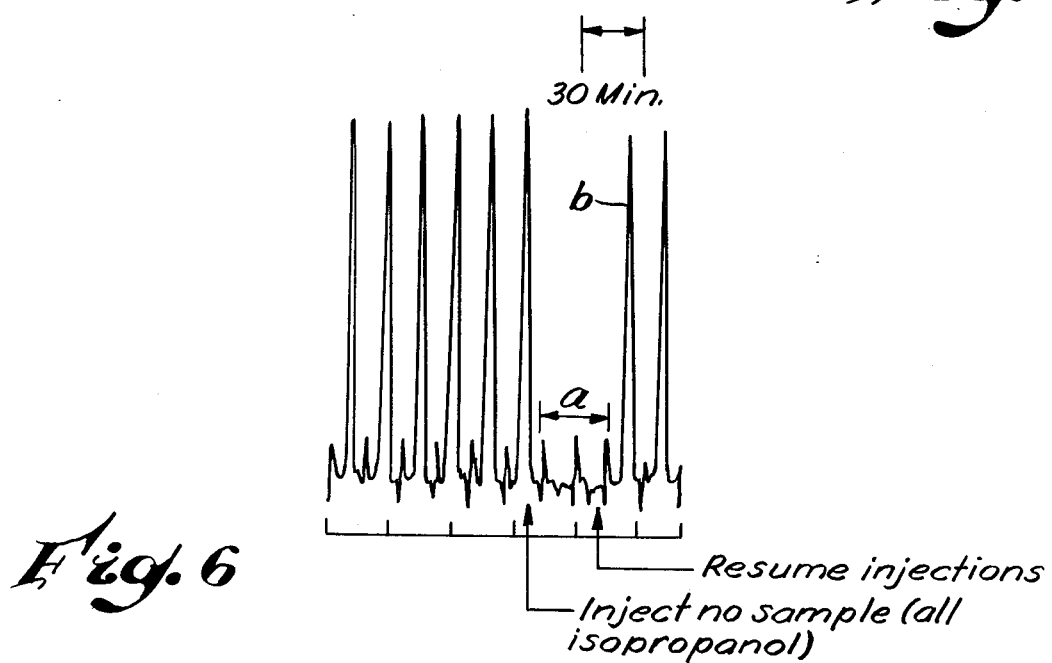

The degree of utility of the described apparatus and technique is illustrated further by reference to the graphs of FIGS. 4 through 6 of the drawing. The specific design illustrated herein produces a precise 320:1 dilution ratio of repeated samples extracted from a process line of 2,4-dichlorophenol, and immersed in isopropyl alcohol diluent. The ratio may be varied from 40:1 to 500:1, or even outside of this extremely broad range, by the simple expedient of selecting the groove size of stem 80, and the size of metering loop 14. Since it is thus mechanically fixed in the equipment, it does not require fine operator adjustments to maintain reliably.

The repeatability is particularly illustrated in the FIG. 4 graph using in combination with the sample preparation system hereof, chromatographic separation and UV detection. The alternate peaks, referred to as the solvent fronts, characteristically are bi-phasic in shape, indicating separation of isopropanol solvent from the sample in the chromatographic column. The following larger peak is the 2,4-dichlorophenol sample. The production of the identical peaks verifies repeatability and precision of the fixed dilution ratio (i.e., little or no erratic behavior within the series of peaks is observed). Based on this data, precision is calculated to be an exceeding satisfactory $\pm 1\%$ ($2\sigma$, is the quantitated standard deviation for 100 peaks). By way of further illustration, it is anticipated that a small amount of diluent is evaporated from the mixing chamber during the course of sample preparation; nevertheless, the loss is seen to be regular and insignificant to the analytical technique.

The graph of FIG. 5 shows confirming data generated with samples consisting of 25 weight percent aqueous sodium chloride solution, diluted in deionized water, using a flow conductivity cell detection system without chromatographic separation. The experiment, the first test of utility of an embodiment of apparatus constructed in accordance with these teachings, again demonstrates satisfactory mixing. That is, since the test is based on flow-through principles, excellent sample mixing is confirmed by the geometry of the peaks (flat top) indicating the uniformity of the salt concentration of the samples, respectively. In addition, the precise uniformity of the peak heights evidences excellent repeatability ofthe fixed sample/diluent ratio, 100:1 in this example (less any diluent evaporation or equivalent regular diluent loss). Since conductivity has been demonstrated to be essentially linear with sodium chloride weight percent in the 250 parts per million (ppm) range utilized the peak uniformity thus validly confirms the precision of the repetitive fixed ratio maintained by the apparatus and technique hereof in this study.

The graph of FIG. 6 involves again the dilution of 2,4-dichlorophenol in isopropyl alcohol, with chromatographic separation and UV detection, and confirms the previous data, showing, with quantitative results, any error as may be due to residual hangup of sample/diluent from the previous cycle. Comparing the major (sample) peaks, prior and subsequent to the injection of NO sample (accomplished by disabling the sample preparation cell, the area of the graph denoted as "a" in the drawing) it is seen that essentially no major or detectable sample peaks remain. Thus, only the diluent peak is produced and remains demonstrating no observed sample hangup problem. Similarly it will be observed that upon resuming the sample/diluent injection, that the thereafter first generated sample peak "b" shows little discrepancy with the preceding peaks. Any discrepancy could properly be ascribed to pure diluent remaining in the system from the previous cycle. However, the consecutive results are extremely representative of the current character of the sample showing little problem with hangup of sample or diluent in the lines. The system thus achieves admirable results without the negative practice of wasting or bypassing diluent to waste systems.

What is claimed is:

1. Method for the batch preparation of analytically useful samples by dilution, said method being distinguished by the steps comprising, pneumatically transferring a metered amount of diluent through a relatively narrow tube into an expanded volume vented mixing chamber to deposit and entrap the diluent in said chamber, whereby the diluent is suspended in the chamber on the head of a moving gas column which produces bubbling agitation as it traverses the trapped diluent, and while in the agitated condition, introducing a metered amount of sample into the chamber and into contact with the agitated diluent to prepare a sample/diluent aliquot of controlled and precisely fixed ratio.

2. The method of claim 1 including the further step of quieting the moving gas column supporting the aliquot and thereafter compressing said column by pneuamatic pressure acting oppositely to said supporting column, to displace the sample into a remote injection loop means.

3. The method of claim 2 including the intermediate step of equilibrating the pneumatic pressures acting oppositely on the aliquot, prior to said displacement step, to remove entrained gas from said sample/diluent aliquot.

4. The method of claim 1, wherein metered sample is introduced into the vented mixing chamber by the steps comprising, routing a continuously flowing sample stream into a position of near proximity to said sample/diluent mixing chamber, and slideably inserting a member from said chamber into said sample stream and extracting therewith a metered volume of sample, which is thusly introduced into the diluent/mixing chamber and into contact with the agitated diluent.

* * * * *

UNITED STATES PATENT AND TRADEMARK OFFICE
CERTIFICATE OF CORRECTION

PATENT NO. : 4,148,610

DATED : April 10, 1979

INVENTOR(S) : Theodore E. Miller, Jr. et al.

It is certified that error appears in the above-identified patent and that said Letters Patent are hereby corrected as shown below:

Col. 4, line 52, delete "vlave" and insert --valve--.

Col. 6, line 8, insert --where: $\sigma$-- after "$2\sigma$,".

Col. 6, line 27, insert a space between the words "of" and "the".

Col. 7, Claim 1, insert at the beginning of line 1, --in combination therewith,-- and delete "while in the agitated condition,".

Col. 7, Claim 1, line 2, delete "and into contact" and insert --,whereby mixing of the sample--.

Col. 7, Claim 1, line 3, insert --is effected-- after the word "diluent", first instance.

Col. 7, Claim 2, line 7, delete "pneuamatic" and insert --pneumatic--.

Col. 8, Claim 4, line 5, delete the comma "," after the word "comprising".

Col. 8, Claim 4, line 10, insert --sample/-- before the word "diluent" and delete the slash "/" after the word "diluent".

UNITED STATES PATENT AND TRADEMARK OFFICE
CERTIFICATE OF CORRECTION

PATENT NO. : 4,148,610

DATED : April 10, 1979

INVENTOR(S) : Theodore E. Miller, Jr. et al.

It is certified that error appears in the above-identified patent and that said Letters Patent are hereby corrected as shown below:

Col. 8, Claim 4, line 11, delete "and into contact with the agitated diluent".

Signed and Sealed this

Seventeenth Day of July 1979

[SEAL]

Attest:

LUTRELLE F. PARKER

Attesting Officer     Acting Commissioner of Patents and Trademarks